United States Patent [19]

Daum

[11] Patent Number: 5,492,514
[45] Date of Patent: Feb. 20, 1996

[54] HOME TRAINER WITH BIOFEEDBACK

[75] Inventor: Wilhelm Daum, Vach, Germany

[73] Assignee: Daum Electronic GmbH, Germany

[21] Appl. No.: 232,770

[22] Filed: Apr. 25, 1994

[30] Foreign Application Priority Data

May 14, 1993 [DE] Germany ............................ 9307352 U

[51] Int. Cl.6 .................................................. A63B 21/00
[52] U.S. Cl. .................................... 482/8; 482/4; 482/57; 482/901; 482/902
[58] Field of Search ....................... 482/1–8, 9, 900–902, 482/57–65; 128/725

[56] References Cited

U.S. PATENT DOCUMENTS

| | | | |
|---|---|---|---|
| 4,170,225 | 10/1979 | Criglar et al. ...................... | 482/900 X |
| 4,367,752 | 1/1983 | Jimenez et al. . | |
| 4,571,682 | 2/1986 | Silverman et al. ................. | 482/901 X |
| 4,776,323 | 10/1988 | Spector ............................... | 482/900 X |
| 4,911,427 | 3/1990 | Matsumoto et al. . | |
| 5,253,168 | 10/1993 | Berg .................................... | 128/725 X |

FOREIGN PATENT DOCUMENTS

| | | |
|---|---|---|
| 3601054 | 7/1987 | Germany . |
| 3908756 | 9/1990 | Germany . |
| 4107323 | 9/1991 | Germany . |
| 1593839 | 7/1981 | United Kingdom . |

*Primary Examiner*—Richard J. Apley
*Assistant Examiner*—Glenn E. Richman
*Attorney, Agent, or Firm*—Laff, Whitesel, Conte & Saret, Ltd.

[57] ABSTRACT

In a home trainer, in particular in the form of a stationary bicycle, a microprocessor and a device for collecting the performance of a person exercising as well as a sensor for detecting the physical condition in dependence on the time during the exercise and after the exercise, provision is made, with a view to achieving an increased psychological stimulus of use even for prolonged periods of time, for sensors being used to measure the electrical resistance of the skin surface, which are connected with a microprocessor, the microprocessor on its part triggering acoustic and/or optical indicator instruments in dependence on the signal received from the sensors.

5 Claims, 1 Drawing Sheet

HOME TRAINER WITH BIOFEEDBACK

BACKGROUND OF THE INVENTION

1. Field of the Invention

The invention relates to a home trainer with biofeedback, in particular in the form of a stationary bicycle, a microprocessor and a device for collecting the performance of a person exercising as well as a sensor for detecting the physical condition in dependence on the time during the exercise and after the exercise being provided on the home trainer.

2. Background Art

The importance of physical fitness has gained considerable importance in the understanding of the general public of late. In this context, numerous home trainers have been developed for instance in the form of rowing devices, but in particular in the form of stationary bicycles, which do not only ensure the performance at home of physical exercise settable in time and in intensity, but which have also been fitted with additional equipment to collect important physical characteristics of the user and, correspondingly, to furnish important information on the physical condition and the training progress, so as to give the exercising person a feeling of achievement through noticeable and measurable training progress and, on the other hand, to allow optimal training build-up from aspects of sports medicine.

The pulse rate of the person exercising was in particular taken as a scale for the physical stress and the recovery rate after termination of the physical stress. Such an instrument has for instance been described in British patent 1,593,839. U.S. Pat. No. 4,367,752 specifies an apparatus for detecting the heart activity comprising a visual indicator and aiming in particular at the exercise of joggers in the open air.

DE 39 08 756 A1 describes a storage unit for controlling an ergometer, allowing the acquisition of data during exercise. DE 26 30 293 B2, too, describes a medical apparatus with a pulse recorder, which ensures an evaluation of the training performance in consideration of specific characteristics of the person exercising. A stationary bicycle comprising a pulse measuring device and data processing for optimizing the training program is described in U.S. Pat. No. 4,911,427. Also DE 36 01 054 A1 and DE 41 07 323 A1 specify apparatuses that ensure proportioning the physical stress and orienting the exercise in consideration of the pulse activty.

The known apparatuses of a concept oriented on sports medicine proceed from the fact that the person exercising will take intense mental interest in the respective data indicated and the training methods, recognizing not only what has to be done for practice, but also having the strong will to do what is required.

In fact, practice has shown that a lot of people take up the exercise with these apparatuses with the intention to make use of the possibilities offered by these apparatuses, but that the exercise is very often discontinued because there is only little psychological stimulus in dealing with such an apparatus alone without any response or whatsoever challenging reaction.

SUMMARY OF THE INVENTION

Proceeding from this, it is the object of the invention to embody a home trainer of the kind mentioned at the outset such that the psychological stimulus of use will be increased even for extended periods of time while the possibility of sensible training from aspects of sports medicine is maintained.

In accordance with the invention this object is solved in that sensors, which are connected with a microprocessor, are provided for measuring the electric resistance of the skin surface, i.e. the so-called psychogalvanic skin effect, the microprocessor on its part triggering acoustic indicator instruments in dependence on the signal received from the sensors.

In keeping with a preferred embodiment it is in particular provided that an acoustic indicator comprises a synthesizer generating a melody which slows down and/or gets deeper in pitch depending on the subsiding of the detected state of excitement.

In another preferred embodiment it is provided that a cassette recorder is arranged on the home trainer additionally or alternatively to the synthesizer, which recorder ensures that cassettes can be inserted on which a training program is stored such that the person exercising gets spoken and/or musically rhythmic instructions on the behavior for exercising.

In this case it is in particular possible, for instance in dependence on fitness characteristics stored from the latest training, to have such programs selected by the microprocessor out of a plurality of stored training programs as will optimally correspond to the actual training condition of the person exercising detected by the microprocessor and the sensors, respectively.

Of course, a compact disk or mini disk reproducer may be used instead of a cassette recorder.

Further details of the invention will become apparent from the ensuing description of a preferred example of embodiment taken in conjunction with the drawing.

DESCRIPTION OF THE PREFERRED EMBODIMENT

Figure 1:
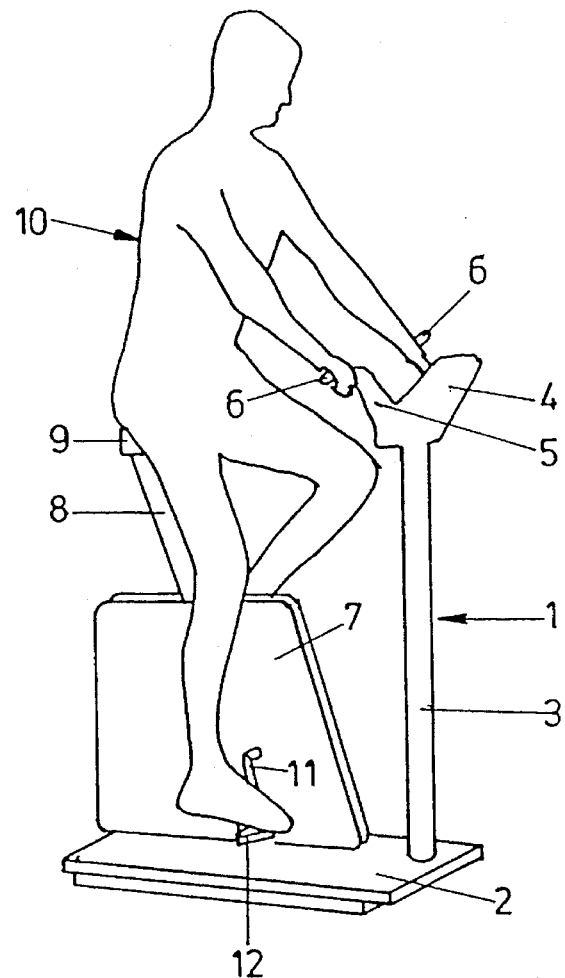
FIG. 1 is a diagramatic representation of a home trainer according to the invention in the form of a stationary bicycle.
Figure 2:
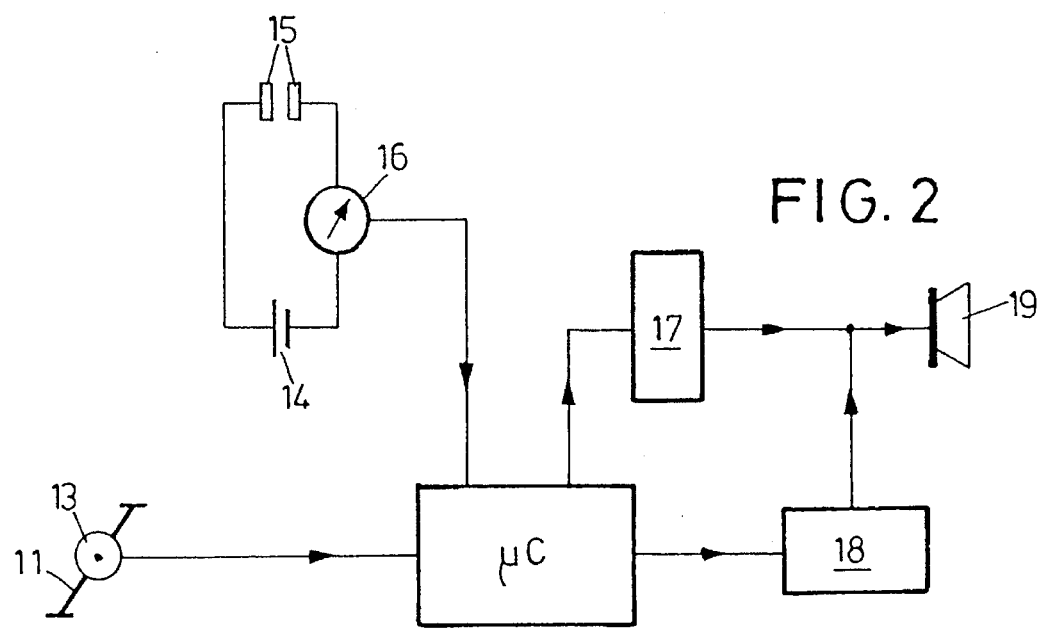
FIG. 2 is a circuit diagram.

FIG. 1 is a diagrammatic representation of a stationary bicycle comprising a base plate 2 on which an upright column 3 is arranged. An indicator panel 4 is provided on the top of the upright column 3. A handle-bar-like arrangement 5 with two handles 6 extends on both sides of the panel 4.

A housing 7 is arranged behind the upright column 3 on the base plate 2, a seat column 8 with a seat 9 for the exercising person 10 extending upwards from the housing 7. Furtheron, a pedal crank arrangement 11 with foot pedals 12 is accommodated in the housing 7. An eddy current brake for adjustably setting the pedal resistance may also be provided in the housing 7 in a manner known per se.

The pedalling performance transferred on the pedals 12 by the exercising person 10 is collected by a measuring device 13 and fed to the input of a microcomputer μC. The so-called psychogalvanic skin effect, i.e. the surface resistance of the skin, is measured and fed to the microcomputer μC by way of a supply terminal 14, sensors 15 and a measuring instrument 16, of which the output is again connected with the microcomputer μC. One output of the microcomputer is connected with a synthesizer 17 and another output with a cassette recorder 18, the outputs of both adjoining a loudspeaker 19.

By reason of the circuit arrangement specified above, it is possible, during the exercise or after termination of the physical exercise, to trigger the synthesizer 17 such that a melody generated by it is deepened in pitch and/or slowed down when the psychogalvanic skin effect goes down, i.e. there is a feedback promotive to the subsiding of the state of excitement conditioned by the exercise, and the person exercising gets an acoustic stimulus.

It is moreover possible to give spoken or musically rhythmic training instructions selected by the microcomputer μC, so that the person exercising is not left alone with his zeal for exercising, but feels motivated and directed.

What is claimed is:

1. A stationary bicycle home trainer, said trainer comprising:

a sensor means, responsive to a physical condition of a person, which detects an electrical resistance of a skin surface of said person, said electrical resistance being dependent on an amount of time during which said person exercises on said trainer and on an amount of time elapsed after which said person stops exercising on said trainer;

a device for collecting, measuring and transmitting data relating to pedaling movements of said trainer;

a microprocessor means connected to said sensor means and said device;

at least one acoustic indicator instrument connected to said microprocessor means wherein said microprocessor triggers said at least one acoustic indicator instrument in response to a signal received from said sensor means, and wherein said at least one acoustic indicator is a reproducer of a medium, said medium being from a group consisting of a cassette, a compact disk, and a mini disk, said medium having a plurality of stored training programs; and a selected training program which gives spoken instructions on the behavior of exercising, said training program being selected from said medium by said microprocessor means in dependence on a training condition of said person exercising, in accordance with fitness characteristics stored from a latest exercise and in dependance on a signal received from said sensors, said sensors checking a physical condition of said person.

2. A stationary bicycle home trainer, said trainer comprising:

a sensor means, responsive to a physical condition of a person, which detects an electrical resistance of a skin surface of said person, said electrical resistance being dependent on an amount of time during which said person exercises on said trainer and on an amount of time elapsed after which said person stops exercising on said trainer;

a device for collecting, measuring and transmitting data relating to pedaling movements of said trainer;

a microprocessor means connected to said sensor means and said device;

at least one acoustic indicator instrument connected to said microprocessor means wherein said microprocessor triggers said at least one acoustic indicator instrument in response to a signal received from said sensor means, and wherein said at least one acoustic indicator is a reproducer of a medium, said medium being from a group consisting of a cassette, a compact disk, and a mini disk, said medium having a plurality of stored training programs, which give spoken instructions on the behavior of exercising;

an interrupt circuit connected to said microprocessor being provided to interrupt a selected training program whenever the microprocessor means detects an exercise condition, said exercise condition being from a group consisting of the following exercise conditions; an exercise condition in which an actual pulse rate of said person is above a first predetermined pulse rate, an exercise condition in which said actual pulse rate of said person is below a second predetermined pulse rate, an exercise condition in which an actual amount of cyclical pedaling motions occurring during a training session exceed a predetermined total amount of cyclical pedaling motions, an exercise condition in which an actual frequency of cyclical pedaling motions occurring during a training session exceed a first predetermined frequency of cyclical pedaling motions, an exercise condition in which the actual frequency of cyclical pedaling motions occurring during a training session is less than a second predetermined frequency of cyclical pedaling motions.

3. A home trainer according to claims 1 or 2 having at least one synthesizer connected to said microprocessor means wherein said microprocessor triggers said synthesizer in response to a signal received from said sensor means, wherein said synthesizer generates a melody which slows down or gets deeper in pitch in dependance on a subsiding of a state of excitement detected by the sensors (15).

4. A home trainer according to claims 1 or 2, wherein at least one reference key is provided for calling training characteristics stored from the latest training exercise and for comparison with stored characteristics of a training cycle actually performed.

5. A stationary bicycle home trainer according to claim 1 or 2 wherein said trainer includes at least one optical indicator instrument being connected to said microprocessor means wherein said microprocessor triggers said at least one optical indicator instrument in response to a signal received from said sensor means.

* * * * *